(12) United States Patent
Khan et al.

(10) Patent No.: US 11,592,433 B2
(45) Date of Patent: Feb. 28, 2023

(54) QUANTIFYING CONTAMINATION OF DOWNHOLE SAMPLES

(71) Applicant: Halliburton Energy Services, Inc., Houston, TX (US)

(72) Inventors: Waqar Ahmad Khan, Houston, TX (US); Mehdi Alipour Kallehbasti, Houston, TX (US); Christopher Michael Jones, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 17/453,556

(22) Filed: Nov. 4, 2021

(65) Prior Publication Data

US 2022/0057380 A1 Feb. 24, 2022

Related U.S. Application Data

(63) Continuation of application No. 16/492,436, filed as application No. PCT/US2017/037975 on Jun. 16, 2017, now Pat. No. 11,215,603.

(51) Int. Cl.
*G01N 33/28* (2006.01)
*E21B 47/06* (2012.01)
(Continued)

(52) U.S. Cl.
CPC ......... *G01N 33/2835* (2013.01); *E21B 47/06* (2013.01); *E21B 47/07* (2020.05);
(Continued)

(58) Field of Classification Search
CPC .. G01N 33/2835; G01N 33/2823; G01N 1/14; E21B 47/07; E21B 47/06;
(Continued)

(56) References Cited

U.S. PATENT DOCUMENTS 6,799,117 B1 9/2004 Proett et al.
7,081,615 B2 7/2006 Betancourt et al.
(Continued)

FOREIGN PATENT DOCUMENTS

WO WO-2005065277 A2 * 7/2005 ............. E21B 49/08
WO 2012103069 A2 8/2012
WO 2012177241 A1 12/2012

OTHER PUBLICATIONS

P.Sah,SPE,Galsep; "Equation-of-State Modeling Reservoir-Fluid Samples Contaminated by Oil-Based Drilling Mud Using Contaminated-Fluid Pressure/Volume; Temperature Data", pp. 139-149 (Year: 2012).*

(Continued)

*Primary Examiner* — Catherine T. Rastovski
*Assistant Examiner* — Kaleria Knox
(74) *Attorney, Agent, or Firm* — DeLizio, Peacock, Lewin & Guerra

(57) ABSTRACT

Systems, devices, and techniques for determining downhole fluid contamination are disclosed. In one or more embodiments, phase-related properties are measured for a reservoir fluid having a determined composition. An equation-of-state (EOS) is selected and/or tuned based, at least in part, on the measured phase-related properties and the tuned EOS is applied to estimate fluid property values for a reference fluid over specified ranges of at least two thermodynamic properties. Contaminant reference data are generated that correlate the estimated fluid property values for the reference fluid with respective contaminant levels. Within a wellbore, a fluid sample is analyzed to determine a fluid property value. A contaminant level is identified that corresponds within the contaminant reference data to the determined fluid property value of the fluid sample.

23 Claims, 6 Drawing Sheets

(51) Int. Cl.
*E21B 49/08* (2006.01)
*E21B 47/07* (2012.01)

(52) U.S. Cl.
CPC ....... *E21B 49/081* (2013.01); *G01N 33/2823* (2013.01); *E21B 49/088* (2013.01); *E21B 49/0875* (2020.05)

(58) Field of Classification Search
CPC .. E21B 49/081; E21B 49/0875; E21B 49/088; E21B 49/10; E21B 49/084; E21B 41/00; E21B 49/00
See application file for complete search history.

(56) References Cited

U.S. PATENT DOCUMENTS

| | | | |
|---|---|---|---|
| 7,372,264 B2 | 5/2008 | Akkurt et al. | |
| 7,637,151 B2 | 12/2009 | Raghuraman et al. | |
| 7,822,554 B2 | 10/2010 | Zho et al. | |
| 8,271,248 B2 | 9/2012 | Pomerantz et al. | |
| 8,434,356 B2 | 5/2013 | Hsu et al. | |
| 8,714,246 B2 | 5/2014 | Pop et al. | |
| 8,744,774 B2 | 6/2014 | Zazovsky | |
| 8,805,617 B2 | 8/2014 | Zuo et al. | |
| 9,029,155 B2 | 5/2015 | Pomerantz et al. | |
| 9,074,460 B2 | 7/2015 | Pomerantz et al. | |
| 9,181,799 B1* | 11/2015 | Harte | E21B 49/084 |
| 2006/0155474 A1* | 7/2006 | Venkataramanan | E21B 49/00 702/6 |
| 2006/0250130 A1 | 11/2006 | Akkurt et al. | |
| 2007/0119244 A1* | 5/2007 | Goodwin | G01N 33/2823 73/152.28 |
| 2007/0137860 A1* | 6/2007 | Lovell | E21B 43/25 166/305.1 |
| 2008/0141767 A1* | 6/2008 | Raghuraman | G01N 33/2823 73/152.55 |
| 2009/0150079 A1* | 6/2009 | Hsu | E21B 49/10 702/11 |
| 2009/0235731 A1 | 9/2009 | Zuo et al. | |
| 2012/0241163 A1* | 9/2012 | Reitsma | E21B 47/06 166/355 |
| 2013/0085674 A1 | 4/2013 | Zhdaneev et al. | |
| 2013/0239671 A1 | 9/2013 | Gisolf et al. | |
| 2013/0312481 A1 | 11/2013 | Pelletier et al. | |
| 2014/0278113 A1 | 9/2014 | Chok et al. | |
| 2015/0136962 A1 | 5/2015 | Pomerantz et al. | |
| 2015/0211363 A1 | 7/2015 | Pop et al. | |
| 2015/0226059 A1* | 8/2015 | Zuo | E21B 49/10 73/152.18 |
| 2016/0319640 A1* | 11/2016 | Ratulowski | E21B 41/00 |
| 2016/0376166 A1* | 12/2016 | Lawryshyn | C02F 1/32 210/709 |
| 2017/0152743 A1* | 6/2017 | Gisolf | G01N 1/14 |

OTHER PUBLICATIONS

French Application Serial No. 1854011; Examination Report; dated Jan. 22, 2019, 3 pages.
International Application No. PCT/US2017/037975, International Search Report dated Mar. 15, 2018, 4 pages.
International Application No. PCT/US2017/037975, Written Opinion dated Mar. 15, 2018, 5 pages.
"Drilling Mud Contamination Analysis", Schlumberger.
"Fundamentals of Formation Testing", Schlumberger; retrieved on Aug. 27, 2019 from https://www.slb.com/-/media/files/fe/book/fundamentals-formation-testing-overview, 2006, 25 pages.
Gozalpour, et al., "Predicting Reservoir Fluid Phase and Volumetric Behavior From Samples Contaminated With Oil-Based Mud", SPE Res Eval & Eng 5 (03): 197-205; Jun. 1, 2002, 5 pages.
Sah, et al., "Equation-of-State Modeling for Reservoir-Fluid Samples Contaminated By Oil-Based Drilling Mud Using Contaminated-Fluid PressureNolume/Temperature Data", Year 2012—Downloaded by PTO on Feb. 2021, 11 pages.
Zuo, et al., "EOS-Based Downhole Fluid Characterization", SPE Asia Pacific Oil and Gas Conference and Exhibition, Oct. 20-22, Perth, Australia, 2008, 8 pages.

* cited by examiner

QUANTIFYING CONTAMINATION OF DOWNHOLE SAMPLES

BACKGROUND

The disclosure generally relates to the field of downhole fluid sampling, and more particularly to quantifying contamination of downhole samples.

Information collected and analyzed during oil and gas exploration may be used to determine the quantity and quality of hydrocarbons in a reservoir and to develop or modify strategies for hydrocarbon extraction. The information may be used for reservoir content evaluation, flow assurance, reservoir stimulation, facility enhancement, production enhancement strategies, and reserve volume estimation. One technique for collecting relevant information involves using a variety of different tools to obtain and analyze fluid samples from a reservoir of interest. The samples may be analyzed to determine fluid properties, including, without limitation, component concentrations, plus fraction molecular weight, gas-oil ratios, bubble point, dew point, phase envelope, viscosity, combinations thereof, or the like. In addition to laboratory analysis, downhole analysis of the fluid sample may also be used to provide real-time fluid properties.

Accurate determination of fluid properties may be problematic as the fluid samples are often contaminated with drilling fluids, such as mud filtrate. The drilling process itself frequently introduces drilling fluid contaminants within a reserve wellbore. A liquid oil-based drilling fluid (alternately referred to as "oil-based mud") is typically comprised of a petroleum base liquid such as diesel. Techniques to determine drilling fluid contamination may include use of pump-out curves, such as density, gas-to-oil ratio and resistivity, among other properties of the fluids. The base liquids used in many oil-based drilling fluids may interfere with determination of the API gravity of the reservoir fluid (i.e., native fluid with the reservoir) due to similarities in properties, particularly fluid densities of the drilling fluid and native reservoir fluid.

BRIEF DESCRIPTION OF THE DRAWINGS

Embodiments of the disclosure may be better understood by referencing the accompanying drawings.

DESCRIPTION

The description that follows includes example systems, methods, techniques, and program flows that embody aspects of the disclosure. However, it is understood that this disclosure may be practiced without these specific details. For instance, this disclosure refers to a system application to quantify downhole contamination of borehole fluid samples that utilize mud filtrate. However, aspects of this disclosure can be also applied to various other types of drilling applications in which the drilling fluid contaminant differs from commonly used mud filtrate. In other instances, well-known structures and techniques have not been shown in detail in order not to obfuscate the description.

The disclosed embodiments provide systems, devices, and techniques for increasing the precision and efficiency in downhole contaminant estimations. Disclosed herein are operations and functions enabling real-time determination of the composition of a formation fluid and/or differentiating between oil-base filtrates and formation fluid hydrocarbons during the process of pumping fluids from a downhole formation. One or more embodiments include a drilling and downhole fluid analysis configuration combined with a computer-based modeling system that tunes an equation-of-state (EOS). The tuned EOS is applied to a reference fluid comprising a reservoir fluid having a specified contaminant level to determine fluid property values over a range of thermodynamic properties.

As utilized herein, an EOS may be generally characterized as a mathematical model or equation that may be used to determine thermodynamic properties and phase equilibrium states for fluids. The disclosed embodiments utilize EOS models to determine thermodynamic fluid properties and behavior of reservoir fluids including reservoir fluids containing well fluid contamination. For example, the Peng-Robinson EOS and the Soave-Redlich-Kwong EOS are commonly utilized in the petroleum industry for oil exploration processes. However, embodiments are not necessarily restricted to any one particular EOS. Without limitation, the EOS may be selected from one or more of Boyle, Van der Waals, Redlich-Kwong, Soave-Redlich-Kwong, Peng-Robinson, Peng-Robinson-Stryjek-Vera, Patek-Teja, Schmidt-Wenzel, and Esmaeilzadeh-Roshanfekr.

Figure 1:
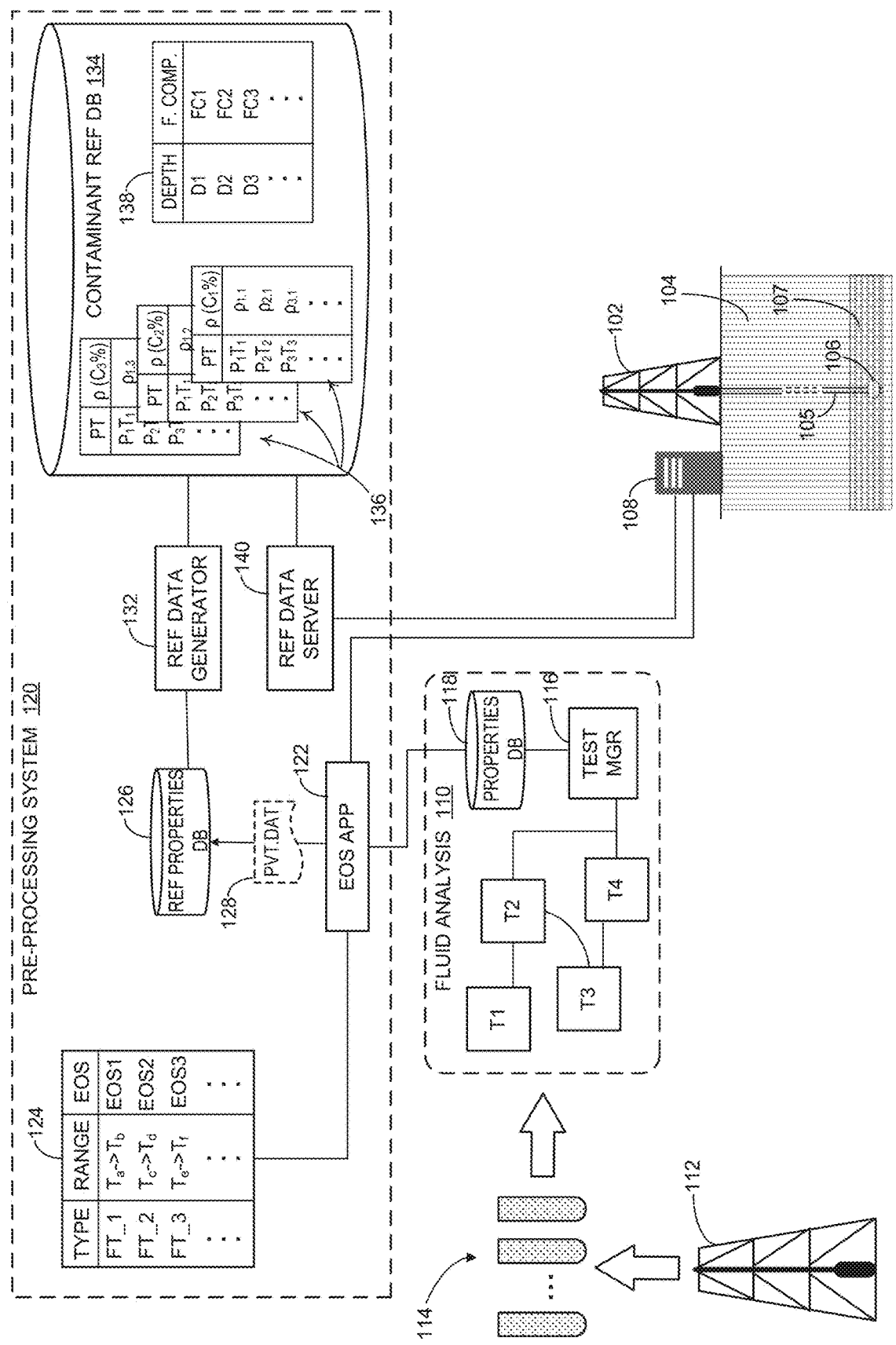
FIG. 1 is a schematic diagram depicting a system for quantifying downhole contamination, according to one or more embodiments.

FIG. 1 is a schematic diagram depicting a system for quantifying downhole contamination, according to one or more embodiments. The system includes an exploratory well apparatus 102 comprising multiple components for drilling an exploratory wellbore 105 within a substrate 104. Exploratory wellbore 105 may be drilled in a geographic region that has not been previously explored or may be drilled in relative proximity (e.g., with 1.5 km) of an existing wellbore in a known petroleum reservoir. During drilling, petroleum content exploration is conducted by the use of a downhole fluid sampling tool 106 that is disposed on a drill string. The downhole fluid sampling tool 106 may be used to obtain a fluid sample, for example, a fluid sample of a reservoir fluid from a subterranean formation 107. The reservoir fluid may be contaminated with well fluid (e.g., oil-based mud as drilling fluid) within wellbore 105. A fluid analytics client 108 may be co-located with well apparatus 102, providing a point of network communication with external systems and devices such as those described below. As described herein, the fluid sample may be analyzed with reference to tuned EOS model data to determine fluid contamination and other fluid properties of the reservoir fluid. As illustrated and typical of exploratory wells, wellbore 105 may extend through subterranean formation 107 substantially vertically.

Accurate determination of hydrocarbon composition is an important aspect of exploratory wells and drilling due, in part, to the considerable resource investment in developing or further developing a region for petroleum extract. To determine hydrocarbon composition, sampling tool 106 is used to measure various reservoir fluid properties such as saturation pressure, density, and gas-to-oil ratio (GOR) that provide indicators of fluid composition. However, the drilling process may introduce contaminants such as the drilling fluid itself within wellbore 105 which may skew the reservoir fluid property measurements. As explained in further detail below, the embodiments disclose systems, devices, components, and techniques for quantifying downhole contamination, particularly for downhole contaminants that are similar in a fluid property such as density to the reservoir fluid for which an accurate composition determination is sought.

The depicted system further includes a well apparatus 112 that may be a production well or other configuration in which drilling fluid contamination has been eliminated or is minimal. In one or more embodiments, exploratory well apparatus 102 is positioned geographically proximate (e.g., within 3 km) to the site at which well apparatus 112 is positioned. In addition to geographic location, other physical and environmental factors may be considered in determining whether sufficient compositional similarity exists or is likely between reservoir fluid sampled by exploratory well apparatus 102 and reservoir fluid extracted and/or sampled from well apparatus 112.

The depicted system further includes a fluid analysis subsystem 110 comprising test modules T1, T2, T3, and T4. Each of the test modules is configured, using any combination of coded software, firmware, and/or hardware, to measure fluid properties of one or more reservoir fluid samples 114 extracted by well apparatus 112. In one or more embodiments, one or more of the test modules may comprise thermodynamic test devices that measure and record PVT properties of reservoir fluid samples such as saturation pressures and densities over a range of pressure/temperature conditions. The test modules may be substantially independent units or may operate in a pipelined manner in which the output of one test module (e.g., T3) may provide at least some input data for subsequent test modules (e.g., T2 and T4).

Fluid analysis subsystem 110 further includes a test manager 116 that receives input directly or indirectly from one or more of test modules T1, T2, T3, and T4. For instance, test manager 116 may receive a series of PVT data points for a particular one or more of reservoir fluid samples 114. Test manager 116 is configured using any combination of software, firmware, and data processing hardware to collect and record measurement result data from the test modules. For example, the measurement result data may be sent to or otherwise retrieved by test manager 116 as encoded data within a series of messages to test manager 116. Test manager 116 is further configured to record the measurement data within record entries associated with respective fluid sample IDs. For example, the record entries may comprise one or more relational tables that are stored in and accessed from a properties database 118.

In one or more embodiments, the measurement data collected and recorded by fluid analysis subsystem 110 is processed with respect to fluid behavioral models to provide contaminant reference data. For example, the system depicted in FIG. 1 includes a pre-processing system 120 comprising programmed code and data processing hardware devices and components for generating contaminant reference data. Pre-processing system 120 includes an EOS application 122 comprising application program code for tuning and applying an EOS in accordance with one or more embodiments. While depicted as a single unit in FIG. 1, the code for tuning an EOS and the code for applying the EOS may comprise different code sets that may or may not partially overlap or be otherwise statically or dynamically linked.

Periodically or in response to a client request, EOS application 122 executes an EOS tuning sequence that may begin with selection of an EOS among multiple available EOS template equations. For example, in response to a client request that specifies a particular reservoir fluid type, EOS application 122 may access an EOS selection table 124 using the specified fluid type as a search index. The EOS template equations (i.e., one or more equation coefficients undetermined) may include Boyle, Van der Waal s, Redlich-Kwong, Soave-Redlich-Kwong, Peng-Robinson, Peng-Robinson-Stryjek-Vera, Patek-Teja, Schmidt-Wenzel, and Esmaeilzadeh-Roshanfekr. As shown, EOS selection table 124 includes three columnar fields, TYPE, RANGE, and EOS, having corresponding field entries that are mutually associated via each row-wise table record having TYPE as the primary index.

Continuing the example, EOS application 122 identifies EOS2 as the subject EOS to be tuned in response to using FT_2 as the primary search index. EOS application 122 may further use a thermodynamic property range as an additional or alternative index in locating and selecting an EOS to be tuned. For instance, EOS application 122 may use FT_3 as a primary index and a minimum and/or maximum temperature value as a secondary index to locate/select EOS3 as the EOS to be tuned. In other embodiments, pressures may be used in addition or alternatively to temperatures as primary or secondary EOS selection indices.

Having selected an EOS template equation, EOS application 122 requests one or more fluid properties records from properties database 118 based, at least in part, on a specified fluid type. The fluid type may correlate to hydrocarbon composition and may be determined by one of the test modules within fluid analysis subsystem 110, or may be specified in the client request, such as from fluid analytics client 108. For instance, based on a reservoir fluid ID presented in the client request, EOS application 122 selects and accesses a record (not depicted) within properties database 118 that associates a set of fluid property values with a fluid ID corresponding directly or indirectly to the requested reservoir fluid ID. The associated property values may include saturation values (e.g., Psat and Tsat), densities at respective temperature and pressure value pairs, GORs at respective temperature and pressure value pairs, etc. EOS application 122 utilizes one or more of the associated property values to tune the selected template EOS. As utilized herein, "tuning" an EOS may be generally characterized as selecting or modifying one or more constant coefficients of the selected EOS.

EOS application 122 tunes the selected EOS by determining and/or modifying at least one constant coefficient value based, at least in part, on the fluid property values retrieved from properties database 118 for reservoir fluid samples that do not contain significant contaminant levels. For example, the selected EOS may be a Peng-Robinson equation of the form:

$$p = \frac{RT}{V_m - b} - \frac{a\alpha}{V_m^2 + 2bV_m - b^2}.$$

This equation solves for fluid density as a function of the universal gas constant, R, temperature, T, molar volume, Vm, and parameter a that depends on temperature, T. In this case, the constant coefficients having values that may be determined or modified include coefficient "a" that depends on critical temperature and pressure parameters in accordance with the equation:

$$a = \frac{0.45724 R^2 T_c^2}{p_c}.$$

The constant coefficients further include coefficient "b" that similarly depends on critical temperature and pressure in accordance with the equation:

$$b = \frac{0.07780 R T_c}{p_c}.$$

For this example, EOS application 122 may utilize temperature and pressure saturation values measured and recorded for the reservoir fluid sample to calculate or otherwise determine values for "a" and/or "b."

As described in further detail with reference to FIG. 2, EOS application 122 applies the tuned EOS to estimate fluid value property values for a reference fluid over specified ranges of thermodynamic parameters (e.g., temperature/ pressure ranges). In one or more embodiments, EOS application 122 executes the tuned EOS using property values for a reference fluid comprising the reservoir fluid and having a specified contaminant level. Preferably, the tuned EOS is executed for multiple reference fluids that each include the same base reservoir fluid and include respectively differing levels of the same contaminant substance. The resulting data comprises PVT property data (e.g., density values) over ranges of expected pressure/temperature conditions. EOS application 122 captures the estimated property values of the reference fluid(s) and sends the data in a PVT data file 128 to be recorded in reference properties database 126.

Pre-processing system 120 further includes a reference data generator 132 comprising any combination of software, firmware, and hardware for generating contaminant reference data. Reference data generator 132 generates the contaminant data based on the estimated reference fluid properties records maintained by and accessible from database 126. For instance, reference data generator 132 may access database 126 using a reference fluid ID as an index to retrieve property values such as density, saturation pressure, and GOR values for a reference fluid. The reference fluid ID may correspond to the fluid ID for the base (i.e., uncontaminated) reservoir fluid. In addition to association with the reservoir fluid type/composition, the property values retrieved from database 126 are associated with one or more respective contamination levels based on the modeling performed using the tuned EOS.

Reference data generator 132 processes the reference fluid property values having respectively associated contamination levels to generate relational tables 136 within a contaminant reference database 134. Each row-wise record of relational tables 136 includes a pressure/temperature field, PT, logically associated with a density field. As shown, the density values in each of tables 136 are specified for the reference fluid having specified contamination levels (specified as different percentages of contamination in the example). Reference data generator 132 may also generate reference fluid property values for the uncontaminated reservoir fluid so that, as explained in further detail with reference to FIG. 3, differences in fluid properties between uncontaminated samples and contaminant influenced models may be pattern-matched with differences detected between downhole samples and reference fluid property values.

If compositional gradient data is available for the reservoir fluid it may be recorded in database 126 in association with the reservoir fluid ID of the reference fluid. Reference data generator 132 may also access the compositional gradient data to generate a compositional gradient table 138 that associates fluid composition data FC1, FC2, and FC3 (e.g., hydrocarbon mole fraction data) with respective reservoir depths D1, D2, and D3.

The system shown in FIG. 1 further includes components for utilizing the contaminant reference data in database 134 during real-time fluid measurements by exploratory well 102 to determine downhole contamination. A reference data server 140 is communicatively connected, such as via network connection, to fluid analytics client 108. Reference data server 140 comprises program code for providing access to contaminant reference data within reference database 134. As depicted and described in further detail with reference to FIG. 3, fluid analytics client 108 communicatively interacts with reference data server 140 to determine downhole contamination by leveraging contamination reference data in combination with real-time measurements of reservoir samples such as which wellbore 105.

Figure 2:
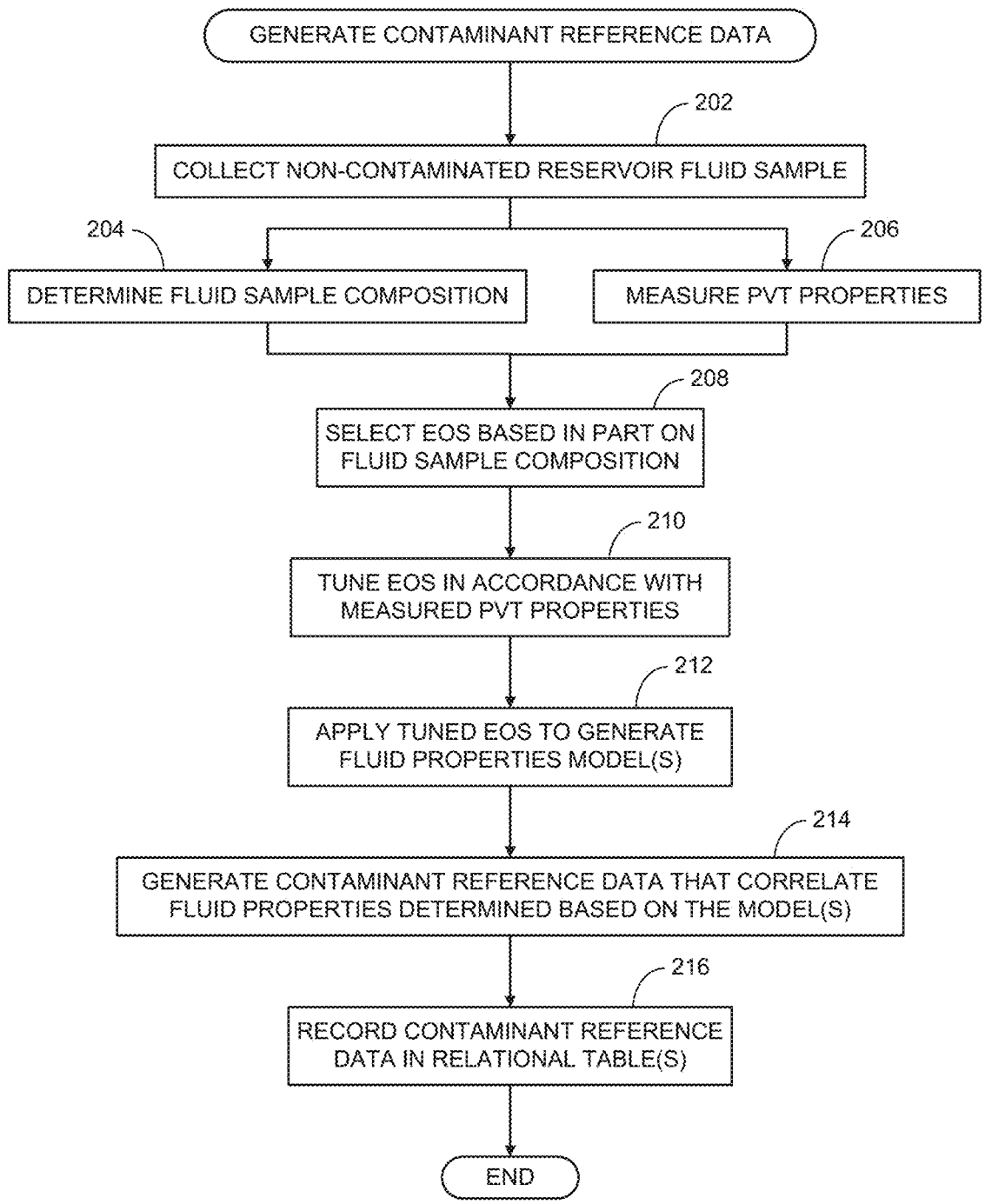
FIG. 2 is a flow diagram illustrating operations and functions for selecting, tuning, and applying an EOS to generate contaminant reference data in accordance with one or more embodiments.

FIG. 2 is a flow diagram illustrating operations and functions for selecting, tuning, and applying an EOS to generate contaminant reference data in accordance with one or more embodiments. The operations and functions depicted in FIG. 2 may be performed by one or more of the systems, devices, and components described with reference to FIG. 1 including fluid analysis subsystem 110, EOS application 122, and reference data generator 132. The process begins as shown at block 202 with a well apparatus used to collect one or more non-contaminated reservoir fluid samples. The well apparatus may be a production well or an infill well that has been established beyond the initial drilling phase that may result in wellbore contamination. The sample(s) may be obtained from regular production in which reservoir fluid is pumped to the surface. Alternatively, the samples may be obtained downhole via use of a downhole sampling tool.

The collected samples are sent to a fluid analysis system comprising multiple testing units that measure phase-related fluid properties of the samples (block 206). The fluid properties may include saturation envelopes, critical points, saturation pressures over temperature ranges, etc. In one or more embodiments, the fluid properties include fluid density over a range of temperature/pressure value pairs. The testing units may include a tool such as a spectroscopy tool that can determine the precise hydrocarbon composition of the samples as shown at block 204.

At block 208, an EOS application selects a non-tuned EOS from among multiple available EOS template equations that may be recorded in a file or table. In one or more embodiments, the EOS is selected based in part on fluid sample composition which may be determined from an associated reservoir fluid ID. The EOS IDs corresponding to respective equations-of-state may be associated within a relational table with specified thermodynamic parameter ranges (e.g., temperature ranges). In such cases, the EOS application may use thermodynamic values (e.g., min and/or max values) in addition to fluid composition to select a particular EOS to be tuned.

At block 210, the EOS application tunes the selected EOS based, at least in part, on fluid properties determined at block 206 including phase-related properties such as critical pressure and temperature and saturation pressure/temperature value pairs. As part of the tuning process, the EOS application matches phase-related property values determined at block 206 with parameters such as coefficient constants in the selected EOS. The EOS application then applies the tuned EOS to estimate fluid property values for one or more reference fluids that each comprise the base reservoir fluid having respective levels of filtrate contamination (block 212). The input parameters processed by the tuned EOS therefore may include ranges of pressure/temperature conditions as well as fluid composition that may be programmatically determined based on the determined reservoir fluid composition and known filtrate compositions. In one or more embodiments, the tuned EOS may be applied to generate fluid density values for a specified reservoir and contaminant composition over a specified temperature/pressure range.

The EOS output is stored in records that associate the reference fluid properties (e.g., fluid densities) with reservoir fluid composition and contamination levels. At blocks 214 and 216 a reference data generator generates contaminant reference data that correlate the estimated fluid property values with respective contaminant levels. For instance, the reference data generator may generate multiple tables that are each associated with a specified contamination level. The records in a given one of the tables associate pressure/temperature value pairs with corresponding densities that were estimated by application of the tuned EOS.

Figure 3:
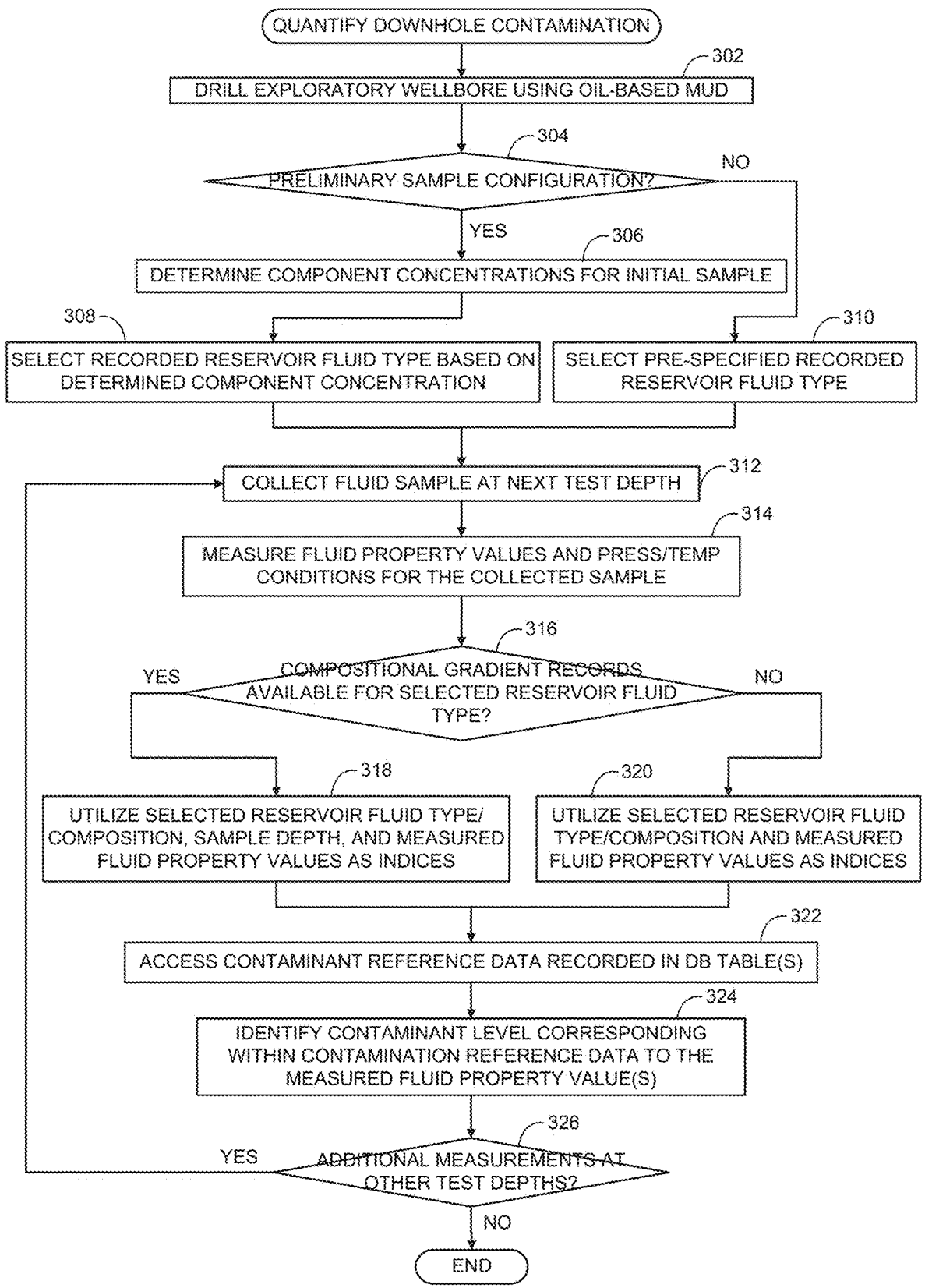
FIG. 3 is a flow diagram depicting operations and functions for quantifying downhole contamination in accordance with one or more embodiments.

FIG. 3 is a flow diagram depicting operations and functions for quantifying downhole contamination in accordance with one or more embodiments. The operations and functions depicted in FIG. 3 may be performed by one or more of the systems, devices, and components described with reference to FIG. 1 including well apparatus 102, downhole sampling tool 106, fluid analytics client 108, and reference data server 140. The process begins as shown at block 302 with an exploratory well apparatus being used to drill an exploratory wellbore using oil-based mud as the drilling fluid. Specifically, the well apparatus drills a borehole into a reservoir formation and during the drilling, oil-based drilling fluid is pumped into the borehole. The drilling fluid serves as a drilling lubricant and coolant in addition to other functions. Oil-based mud may include such as diesel or other oil as a filtrate fluid.

The well apparatus includes a fluid sampling tool that may be configured to collect and analyze an initial/preliminary sample of the reservoir fluid to determine its carbon composition. If the sampling tool is so configured, (block 304) the sampling tool determines component concentrations for an initial sample (block 306). At block 308, a fluid analytics tool communicatively connected to the sampling tool selects a reservoir fluid type based on the composition of the initial sample. If, at block 304, the sampling tool is not configured to collect and analyze an initial/preliminary sample of the reservoir fluid to determine its carbon composition, a fluid analytics client selects a reservoir fluid type that has been pre-specified (block 310).

Following selection of a reservoir fluid type (e.g., fluid ID associated with a specified fluid composition), the sampling tool continues collecting fluid samples at various sub-terrain depths (block 312) within a wellbore/borehole. The sampling tool is configured to include one or more sensors for measuring properties of the fluid sample (block 314) such as saturation pressure, GOR, density, etc. In addition to the means for selecting the reservoir fluid type at blocks 308 and 310, the system may include or have access to compositional gradient data that can modify the selected fluid type based on the depth at which the sampling tool is collecting samples and measuring fluid properties (block 316). If so, the fluid analytics client in combination with a reference data server utilize the selected fluid type/composition in combination with the sample depth and measured fluid properties as indices into the contaminant reference data that may be stored as relational tables in a contaminant reference database (block 318). If compositional gradient data is not available, fluid analytics client and reference data server utilize the selected fluid type/composition in combination with the measured fluid properties as indices into the contaminant reference data that may be stored as relational tables in a contaminant reference database (block 320).

At block 322, the reference data server accesses contaminant reference data within the database/table using a correspondence between the measured fluid sample and like parameters in the contaminant reference data. For example, the reference data server may use the value of a measured fluid property in addition to temperature and pressure conditions for the sample as indices to select a corresponding record within the contaminant reference data. At block 324, the reference data server and/or the fluid analytics client identify a contaminant level that corresponds, within the contaminant reference data, to at least one of the measure fluid property values. In one or more embodiments, the contaminant level may be identified by comparing a measured fluid property value (e.g., fluid density at sampled pressure/temperature) with a corresponding fluid property value that was estimated by the turned EOS (e.g., fluid density at sampled pressure/temperature). In response to detecting a sufficient difference (e.g., exceeding a specified threshold) between the values, the fluid analytics client determines whether a specified pattern match (e.g., magnitude or direction) exists between the detected difference and a difference between the estimated reference fluid value and an estimated property value for the same base fluid without contamination. If a pattern match exists, the reference data value is accepted as correct and corresponding contaminant level identified at block 324. Control passes from block 326 back through blocks 312-324 until the exploratory sampling is complete and the process ends.

Figure 4:
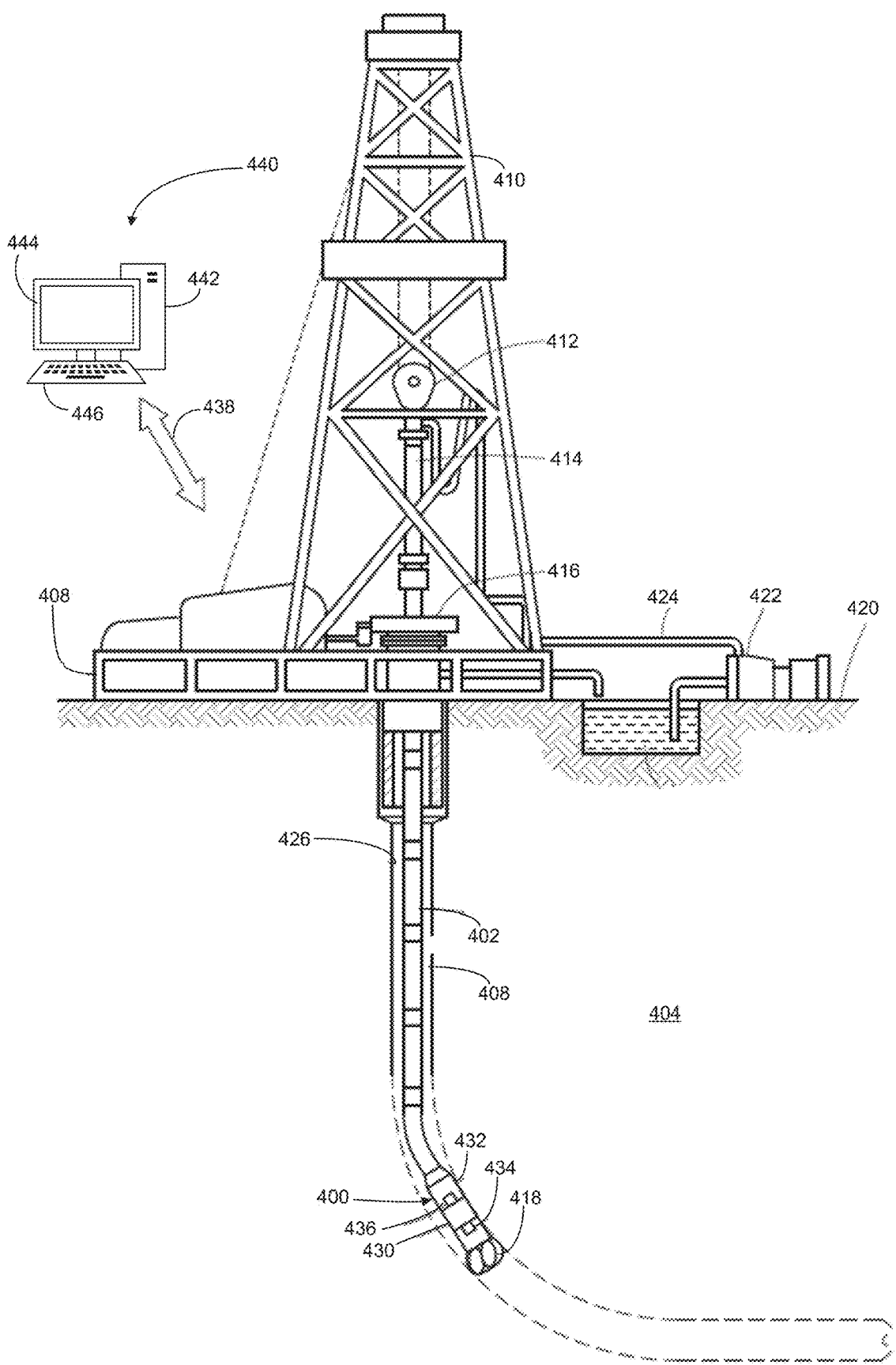
FIG. 4 depicts a schematic diagram of a wellbore sampling and analysis system, according to one or more embodiments.

FIG. 4 is a schematic diagram of an apparatus that can be used to perform some of the operations and functions described with reference to FIGS. 1-3. The apparatus includes a downhole fluid sampling tool 400 disposed on a drill string 402 of a depicted well apparatus. Fluid sampling tool 400 may be used to obtain a fluid sample such as a sample of a reservoir fluid from a subterranean formation 404. The reservoir fluid may be contaminated with well fluid (e.g., drilling fluid) from wellbore 406. While wellbore 406 is shown extending generally vertically into the subterranean formation 404, the principles described herein are also applicable to wellbores that extend at an angle through the subterranean formation 404, such as horizontal and slanted wellbores. For example, although FIG. 4 shows a vertical or low inclination angle well, high inclination angle or horizontal placement of the well and equipment is also possible. It should further be noted that while FIG. 4 generally depicts a land-based operation, those skilled in the art will readily recognize that the principles described herein are equally applicable to subsea operations that employ floating or sea-based platforms and rigs, without departing from the scope of the disclosure.

The well apparatus further includes a drilling platform 408 that supports a derrick 410 having a traveling block 412 for raising and lowering drill string 402. Drill string 402 may include, but is not limited to, drill pipe and coiled tubing, as generally known to those skilled in the art. A kelly 414 may support drill string 402 as it may be lowered through a rotary table 416. A drill bit 418 may be attached to the distal end of drill string 402 and may be driven either by a downhole motor and/or via rotation of drill string 402 from the surface 420. Without limitation, drill bit 418 may include, roller cone bits, PDC bits, natural diamond bits, any hole openers, reamers, coring bits, and the like. As drill bit 418 rotates, it may create and extend wellbore 406 that penetrates various subterranean formations such as 404. A pump 422 may circulate drilling fluid through a feed pipe 424 to kelly 414, downhole through interior of drill string 402, through orifices in drill bit 418, back to surface 420 via annulus 426 surrounding drill string 402, and into a retention pit 428.

Drill bit 418 may be just one piece of a downhole assembly that may include one or more drill collars 430 and sampling tool 400. Sampling tool 400, which may be built into drill collars 430, may gather measurements and fluid samples as described herein. One or more drill collars 430 may form a tool body 432, which may be elongated as shown on FIG. 4. Tool body 432 may be any suitable material, including without limitation titanium, stainless steel, alloys, plastic, combinations thereof, and the like. Sampling tool 400 may further include one or more sensors 434 for measuring properties of the fluid sample, reservoir fluid, wellbore 406, subterranean formation 404, or the like. As previously described, fluid samples collected by sampling tool 400 may comprise a reservoir fluid, which may be contaminated with a well fluid.

Sampling tool 400 may further include a fluid analysis module 436 configured and operable to derive properties and characterize the fluid sample. For example, fluid analysis module 436 may measure absorption spectra and translate such measurements into component concentrations of the fluid sample, which may be lumped component concentrations, as described above. Fluid analysis module 436 may also measure gas-to-oil ratio, live fluid density, live fluid viscosity, formation pressure, and formation temperature. Fluid analysis module 436 may also be operable to determine fluid contamination of the fluid sample. Fluid analysis module 436 include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, fluid analysis module 436 may include random access memory (RAM), one or more processing units, such as a central processing unit (CPU), or hardware or software control logic, ROM, and/or other types of nonvolatile memory.

Any suitable technique may be used for transmitting signals from sampling tool 400 to a computing system residing on the surface 420. As illustrated, a communication link 438 (which may be wired or wireless, for example) may be provided that may transmit data from sampling tool 400 to an information handling system 440 at surface 420. Communication link 438 may implement one or more of various known drilling telemetry techniques such as mud-pulse, acoustic, electromagnetic, etc. Information handling system 440 may include a processing unit 442, a monitor 444, an input device 446 (e.g., keyboard, mouse, etc.), and/or computer media 448 (e.g., optical disks, magnetic disks) that can store code representative of the methods described herein. Information handling system 440 may act as a data acquisition system and possibly a data processing system that analyzes information from sampling tool 400. For example, information handling system 440 may process the information from sampling tool 400 for determination of fluid contamination. Information handling system 440 may also determine additional properties of the fluid sample (or reservoir fluid), such as component concentrations, pressure-volume-temperature properties (e.g., bubble point, phase envelop prediction, etc.) based on the fluid characterization. This processing may occur at surface 420 in real-time. Alternatively, the processing may occur at surface 420 or another location after withdrawal of sampling tool 400 from wellbore 406. Alternatively, the processing may be performed by an information handling system in wellbore 406, such as fluid analysis module 436. The resultant fluid properties may then be transmitted to surface 420, for example, in real-time to a fluid analytics client running on information handling system 440.

Figure 5:
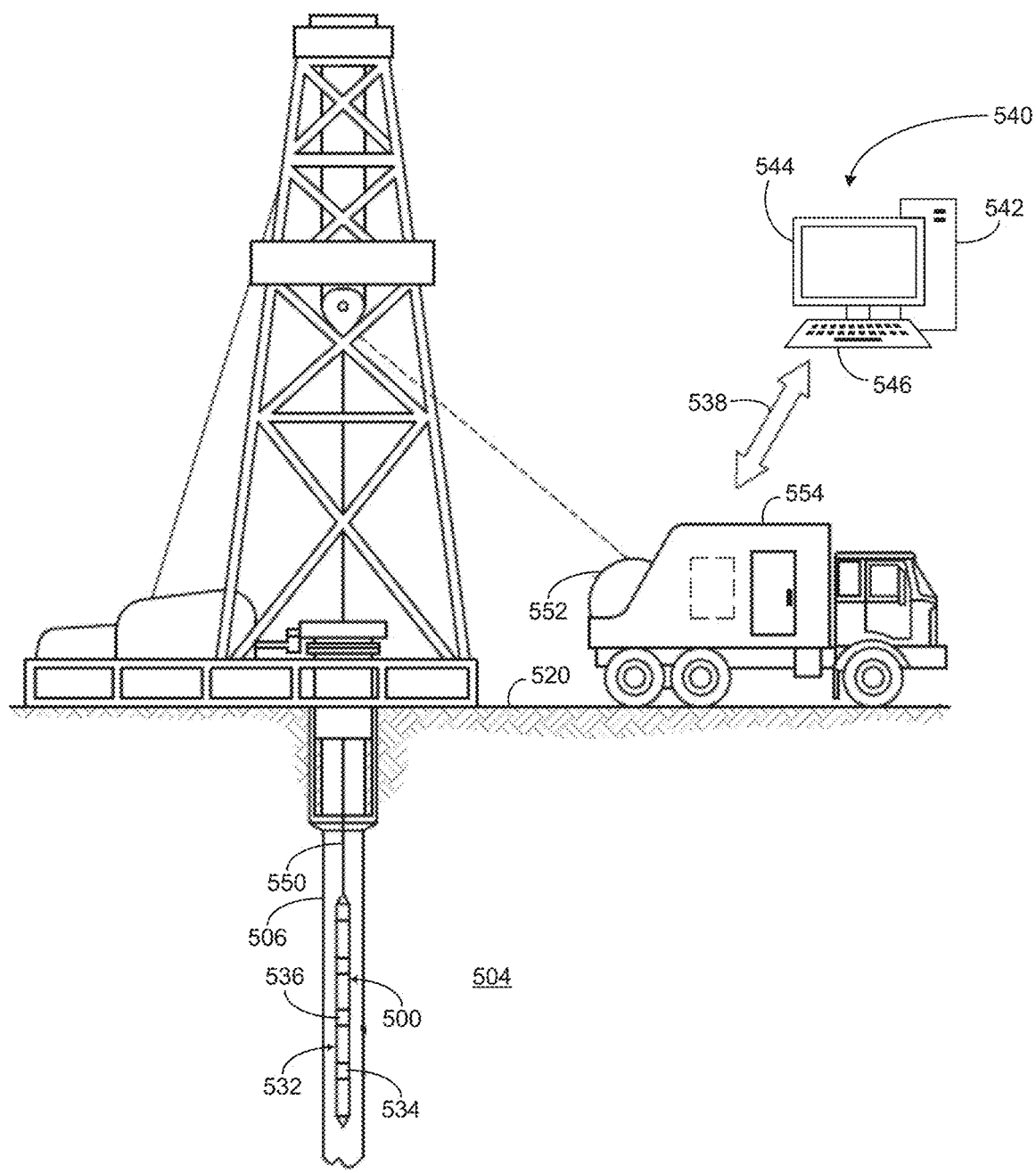
FIG. 5 is a schematic diagram of an example downhole fluid sampling and analysis tool on a wireline according to one or more embodiments.

Referring now to FIG. 5, a schematic diagram is shown of downhole fluid sampling tool 500 on a wireline 550. As illustrated, a wellbore 506 may extend through subterranean formation 504. Downhole fluid sampling tool 500 may be similar in configuration and operation to downhole fluid sampling tool 400 shown on FIG. 4 except that FIG. 5 shows downhole fluid sampling tool 500 disposed on wireline 550. It should be noted that while FIG. 5 generally depicts a land-based drilling system, those skilled in the art will readily recognize that the principles described herein are equally applicable to subsea drilling operations that employ floating or sea-based platforms and rigs, without departing from the scope of the disclosure.

As illustrated, a hoist 552 may be used to run sampling tool 500 into wellbore 506. Hoist 552 may be disposed on a recovery vehicle 554. Hoist 552 may be used, for example, to raise and lower wireline 550 in wellbore 506. While hoist 552 is shown on recovery vehicle 554, it should be understood that wireline 550 may alternatively be disposed from a hoist 552 that is installed at surface 520 instead of being located on recovery vehicle 554. Downhole fluid sampling tool 500 may be suspended in wellbore 506 on wireline 550. Other conveyance types may be used for conveying downhole fluid sampling tool 500 into wellbore 506, including coiled tubing, wired drill pipe, slickline, and downhole tractor, for example. Downhole fluid sampling tool 500 may comprise a tool body 532, which may be elongated as shown on FIG. 5. Tool body 532 may be any suitable material, including without limitation titanium, stainless steel, alloys, plastic, combinations thereof, and the like. Downhole fluid sampling tool 500 may further include one or more sensors 534 for measuring properties of the fluid sample, reservoir fluid, wellbore 506, subterranean formation 504, or the like. The downhole fluid sampling tool 500 may also include a fluid analysis module 536, which may be operable to process information regarding fluid sample, as described above with respect to FIGS. 1, 3, and 5. The downhole fluid sampling tool 500 may be used to collect fluid samples from subterranean formation 504. The downhole fluid sampling tool 500 may obtain and separately store different fluid samples from subterranean formation 504.

As previously described, information from sampling tool 500 may be transmitted to an information handling system 540, which may be located at surface 520. As illustrated, communication link 538 (which may be wired or wireless, for example) may be provided that may transmit data from downhole fluid sampling tool 500 to an information handling system 540 at surface 520. Information handling system 540 may include a processing unit 542, a monitor 544, an input device 546 (e.g., keyboard, mouse, etc.), and/or computer media 548 (e.g., optical disks, magnetic disks) that can store code representative of the methods described herein. In addition to, or in place of processing at surface 520, processing may occur downhole (e.g., fluid analysis module 536).

Figure 6:
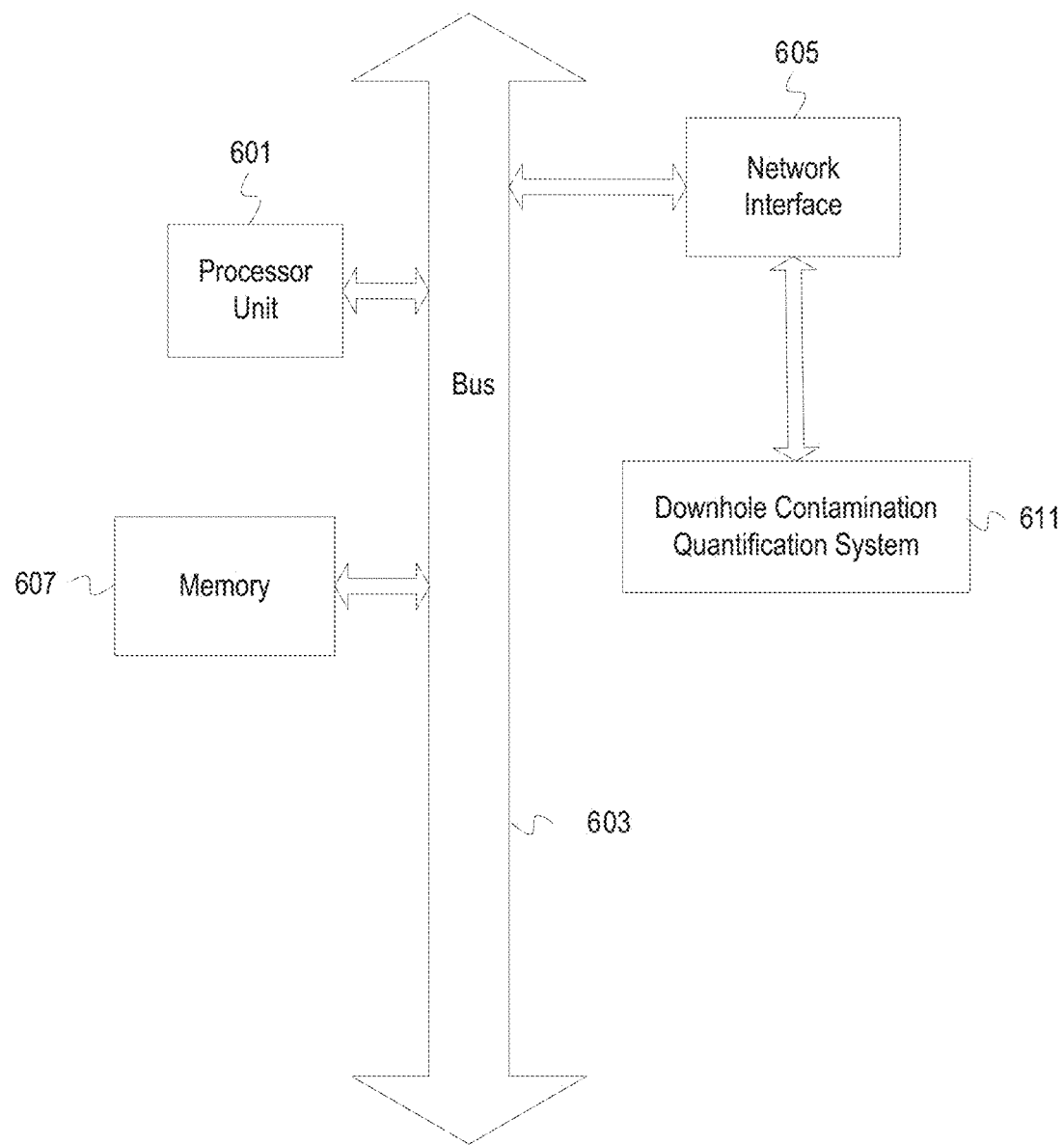
FIG. 6 depicts an example computer system that implements contaminant quantification according to one or more embodiments.

FIG. 6 depicts an example computer system, according to one or more embodiments, that may implement one or more or all of the operations and functions described with reference to FIGS. 1-5 such as those performed by information handling system 640 in FIG. 6. The computer system includes a processor 601 (possibly including multiple processors, multiple cores, multiple nodes, and/or implementing multi-threading, etc.). The computer device includes memory 607. The memory 607 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media.

The computer system also includes a persistent data storage 609. The persistent data storage 609 can be a hard disk drive, such as magnetic storage device. The computer device also includes a bus 603 (e.g., PCI, ISA, PCI-Express, HyperTransport® bus, InfiniBand® bus, NuBus, etc.) and a network interface 605 (e.g., a Fiber Channel interface, an Ethernet interface, an internet small computer system interface, SONET interface, wireless interface, etc.).

The computer system also includes a downhole contamination quantification system 611 connected to bus 603 via network interface 605. The contamination quantification system 611 can perform a variety of fluid sampling and analysis operations as well as performing operations for tuning and applying an EOS to generate reference fluid data, as described above. Any one of the previously described functionalities may be partially (or entirely) implemented in hardware and/or on the processor 601. For example, the functionality may be implemented with an application specific integrated circuit, in logic implemented in the processor 601, in a co-processor on a peripheral device or card, etc. Further, realizations may include fewer or additional components not illustrated in FIG. 6 (e.g., video cards, audio cards, additional network interfaces, peripheral devices, etc.).

The flowcharts are provided to aid in understanding the illustrations and are not to be used to limit scope of the claims. The flowcharts depict example operations that can vary within the scope of the claims. Additional operations may be performed; fewer operations may be performed; the operations may be performed in parallel; and the operations may be performed in a different order. It will be understood that at least one or more of blocks of the flowchart illustrations and/or block diagrams, and combinations of blocks in the flowchart illustrations and/or block diagrams, can be implemented by program code. The program code may be provided to a processor of a general purpose computer, special purpose computer, or other programmable machine or apparatus.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine-readable medium(s) may be utilized herein. The machine-readable medium may be a machine readable signal medium or a machine readable storage medium. A machine readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine readable storage medium may be any tangible medium that can contain, or store a program for use by or in connection with an instruction execution system, apparatus, or device. A machine readable storage medium is not a machine readable signal medium.

A machine readable signal medium may include a propagated data signal with machine readable program code embodied therein, for example, in baseband or as part of a carrier wave. Such a propagated signal may take any of a variety of forms, including, but not limited to, electromagnetic, optical, or any suitable combination thereof. A machine readable signal medium may be any machine readable medium that is not a machine readable storage medium and that can communicate, propagate, or transport a program for use by or in connection with an instruction execution system, apparatus, or device.

Program code embodied on a machine readable medium may be transmitted using any appropriate medium, including but not limited to wireless, wireline, optical fiber cable, RF, etc., or any suitable combination of the foregoing. Computer program code for carrying out operations for aspects of the disclosure may be written in any combination of one or more programming languages, including an object oriented programming language such as the Java® programming language, C++ or the like; a dynamic programming language such as Python; a scripting language such as Perl programming language or PowerShell script language; and conventional procedural programming languages, such as the "C" programming language or similar programming languages. The program code may execute entirely on a stand-alone machine, may execute in a distributed manner across multiple machines, and may execute on one machine while providing results and or accepting input on another machine.

The program code/instructions may also be stored in a machine readable medium that can direct a machine to function in a particular manner, such that the instructions stored in the machine readable medium produce an article of manufacture including instructions which implement the function/act specified in the flowchart and/or block diagram block or blocks.

While the aspects of the disclosure are described with reference to various implementations and exploitations, it will be understood that these aspects are illustrative and that the scope of the claims is not limited to them.

Example Embodiments

Embodiments generally include a method that determines downhole fluid contamination. The method comprises measuring phase-related properties for a reservoir fluid having a determined composition and tuning an equation-of-state (EOS) based, at least in part, on the phase-related properties. The method further comprises applying the tuned EOS to estimate fluid property values for a reference fluid over specified ranges of at least two thermodynamic properties, and generating contaminant reference data that correlate the estimated fluid property values for the reference fluid with respective contaminant levels. The method further includes steps performed within a wellbore including collecting a fluid sample, determining a fluid property value for the fluid sample, and identifying a contaminant level that corresponds within the contaminant reference data to the determined fluid property value of the fluid sample.

In one or more embodiments, the reference fluid comprises the reservoir fluid having a specified contaminant level and the method further includes applying the tuned EOS to estimate fluid property values for the reservoir fluid over the specified ranges of at least two thermodynamic properties. In one or more embodiments, the identification of a contaminant level includes, in response to detecting a difference between the fluid property value for the fluid sample and an estimated fluid property value for the reservoir fluid that is associated with a temperature and pressure at which the fluid property sample was collected, detecting a pattern match between the detected difference and a difference between a fluid property value estimated for the reference fluid and a fluid property value estimated for the reservoir fluid. The method may further include in response to the detected pattern match, identifying a contamination level that corresponds to the fluid property estimated for the reference fluid.

In one or more embodiments, the method further includes obtaining a sample of the reference fluid by collecting reservoir fluid from a reservoir from which the reservoir fluid was obtained, and adding a specified amount of contaminant to the collected reservoir fluid to form a contaminated reference fluid sample. In one or more embodiments, applying the tuned EOS to estimate fluid property values for the reference fluid comprises applying the tuned EOS to estimate fluid property values for the contaminated reference fluid sample.

In one or more embodiments, the method further comprises associating the tuned EOS with a reservoir fluid ID corresponding to the reservoir fluid and with a reference fluid ID associated with the reference fluid.

In one or more embodiments, the measuring of phase-related properties comprises determining multiple saturation pressure values for each of multiple saturation temperature values.

In one or more embodiments, generating contaminant reference data comprises generating relational tables that associate each of multiple fluid composition types with a correlated set of fluid property values and corresponding contaminant levels. In one or more embodiments the identifying of a contaminant level may comprise selecting, based at least in part on compositional gradient data in combination with a determined sample depth, a fluid composition type, and utilizing the selected fluid composition type as an input to access a correlated set of fluid property values and corresponding contaminant levels.

In one or more embodiments, the tuning of the EOS comprises determining at least one coefficient value based, at least in part, on the measured phase-related properties.

In one or more embodiments, the method further comprises associating the identified contaminant level with a fluid sample identifier (ID) of the collected fluid sample. In one or more embodiments, the method further comprising selecting the EOS from among multiple equations-of-state based, at least in part, on an input range of thermodynamic values Any of the example embodiments described above may be realized as a system, a method, program code on machine readable media, or as an apparatus. Additional embodiments can include varying combinations of features or elements from the example embodiments described above. For example, one embodiment may include elements from three of the example embodiments while another embodiment includes elements from five of the example embodiments described above.

The invention claimed is:

1. A method comprising:
   measuring fluid property values for a first wellbore fluid obtained at a first sample depth in a wellbore, wherein the first wellbore fluid comprises at least one of a reservoir fluid and a first contaminant;
   selecting an equation-of-state from among multiple equations-of-state based, at least in part, on an input range of thermodynamic values;
   tuning the equation-of-state based, at least in part, on the fluid property values; and
   determining a fluid composition value of the first wellbore fluid based, at least in part, on the tuned equation-of-state.

2. The method of claim 1, wherein the fluid composition value is a contamination level.

3. The method of claim 1, further comprising:
   generating contaminant reference data based, at least in part, on the measured fluid property values for the first wellbore fluid and the determined fluid composition value of the first wellbore fluid, wherein the contaminant reference data correlates fluid property values to fluid composition.

4. The method of claim 3, wherein the contaminant reference data further correlates fluid property values and fluid composition to at least one of sample depth in the wellbore, fluid pumpout volume and fluid pumpout time.

5. The method of claim 3, further comprising:
   measuring fluid property values for a second wellbore fluid obtained at a second sample depth in a wellbore, wherein the second wellbore fluid comprises at least one of a reservoir fluid and a second contaminant; and
   determining a fluid composition of the second wellbore fluid based, at least in part, on the tuned equation-of-state and the contaminant reference data.

6. The method of claim 5, wherein determining the fluid composition of the second wellbore fluid further comprises:
   tuning the equation-of-state based, at least in part, on the measured fluid property values of the second wellbore fluid.

7. The method of claim 6, wherein tuning the equation-of-state comprises selecting the equation-of-state based, from among multiple equations-of-state based, at least in part, on an input range of thermodynamic values for the second wellbore fluid.

8. The method of claim 5, further comprising:
updating the contaminant reference data based, at least in part, on the measured fluid property values for the second wellbore fluid and the determined fluid composition of the second wellbore fluid.

9. The method of claim 8, further comprising determining an updated fluid composition value of the first wellbore fluid based, at least in part, on the updated contaminant reference data.

10. The method of claim 5, wherein the first sample depth is the second sample depth.

11. The method of claim 5, wherein the second contaminant comprises the first contaminant.

12. The method of claim 5, further comprising:
determining a compositional gradient based, at least in part, on the fluid composition of the first wellbore fluid and the fluid composition of the second wellbore fluid.

13. A non-transitory, machine-readable medium having instructions stored thereon that are executable by a computing device to perform operations comprising:
obtain fluid property values for a first wellbore fluid sampled at a first depth in a wellbore, wherein the first wellbore fluid comprises at least one of a reservoir fluid and a first contaminant;
select a first equation-of-state from among multiple equations-of-state based, at least in part, on an input range of thermodynamic values;
tune the first equation-of-state based, at least in part, on the fluid property values; and
determine a fluid composition value for the first wellbore fluid based, at least in part, on the tuned first equation-of-state.

14. The non-transitory, machine-readable medium of claim 13, further comprising instructions to:
correlate the fluid property values for the first wellbore fluid and the fluid composition value for the first wellbore fluid; and
generate contaminant reference data based, at least in part, on the correlation.

15. The non-transitory, machine-readable medium of claim 14, further comprising instructions to:
obtain fluid property values for a second wellbore fluid sampled at a second depth in a wellbore, wherein the second wellbore fluid comprises at least one of a reservoir fluid and a second contaminant; and
determine a fluid composition value for the second wellbore fluid based, at least in part, on the contaminant reference data.

16. The non-transitory, machine-readable medium of claim 15, further comprising instructions to:
correlate the fluid property values for the second wellbore fluid and the fluid composition value for the second wellbore fluid; and
update the contaminant reference data based, at least in part, on the correlation for the second wellbore fluid.

17. The non-transitory, machine-readable medium of claim 15, further comprising instructions to:
determine a compositional gradient based, at least in part, on the fluid composition value of the first wellbore fluid and the fluid composition value of the second wellbore fluid and at least one of
a difference between a fluid pumpout volume for the first wellbore fluid and a fluid pumpout volume for the second wellbore fluid,
a difference between a fluid pumpout time for the first wellbore fluid and a fluid pumpout time for the second wellbore fluid;
obtain fluid property values for a third wellbore fluid sampled at a third depth in a wellbore, wherein the third wellbore fluid comprises at least one of a reservoir fluid and a third contaminant; and
estimate a fluid composition value for the third wellbore fluid based, at least in part, on the compositional gradient and at least one of a fluid pumpout volume for the third wellbore fluid and a fluid pumpout time for the third wellbore fluid.

18. The non-transitory, machine-readable medium of claim 17, further comprising instructions to:
determine a fluid composition value for the third wellbore fluid based, at least in part, on the contaminant reference data; and
determine whether a difference the estimated fluid composition value for the third wellbore fluid to the determined fluid composition value for the third wellbore fluid exceeds a threshold; and
based on a determination that the difference exceeds the threshold,
correlate the fluid property values for the third wellbore fluid and the fluid composition value for the third wellbore fluid; and
update the contaminant reference data based, at least in part, on the correlation for the third wellbore fluid.

19. The non-transitory, machine-readable medium of claim 15, further comprising instruction to:
obtain fluid property values for a third wellbore fluid sampled at a third depth in a wellbore, wherein the third wellbore fluid comprises at least one of a reservoir fluid and a third contaminant; and
determine a fluid composition value for the third wellbore fluid based, at least in part, on the contaminant reference data and at least one of a fluid pumpout volume for the third wellbore fluid and a fluid pumpout time for the third wellbore fluid,
wherein instructions to correlate the fluid property values for the first wellbore fluid and the fluid composition value for the first wellbore fluid further comprise instruction to correlate the fluid property values for the first wellbore fluid and the fluid composition value for the first wellbore fluid to at least one of a fluid pumpout volume for the first wellbore fluid and a fluid pumpout time for the first wellbore fluid,
wherein instructions to correlate the fluid property values for the second wellbore fluid and the fluid composition value for the second wellbore fluid further comprise instruction to correlate the fluid property values for the second wellbore fluid and the fluid composition value for the second wellbore fluid to at least one of a fluid pumpout volume for the second wellbore fluid and a fluid pumpout time for the second wellbore fluid.

20. The non-transitory, machine-readable medium of claim 15, wherein instruction to determine the fluid composition value for the second wellbore fluid comprise instruction to:
select a second equation-of-state from among multiple equations-of-state based, at least in part, on an input range of thermodynamic values for the second wellbore fluid;
tune the second equation-of-state based, at least in part, on the fluid property values for the second wellbore fluid; and
determine a fluid composition value for the second wellbore fluid based, at least in part, on the contaminant reference data and the tuned second equation-of-state.

21. A system, comprising:
a wellbore sampling system, wherein the wellbore sampling system obtains at least one wellbore fluid sample;
a fluid analysis system, wherein the fluid analysis system measures at least one fluid property for the at least one wellbore fluid sample;
a processor; and
a machine-readable medium having program code executable by the processor to cause the system to:
obtain fluid property values for a first wellbore fluid sampled at a first depth in a wellbore, wherein the first wellbore fluid comprises at least one of a reservoir fluid and a first contaminant;
select a first equation-of-state from among multiple equations-of-state based, at least in part, on an input range of thermodynamic values;
tune the first equation-of-state based, at least in part, on the fluid property values; and
determine a fluid composition value for the first wellbore fluid based, at least in part, on the tuned first equation-of-state.

22. The system of claim 21, further comprising machine-readable medium having program code executable by the processor to cause the system to:
correlate the fluid property values for the first wellbore fluid and the fluid composition value for the first wellbore fluid; and
generate contaminant reference data based, at least in part, on the correlation.

23. The system of claim 22, further comprising machine-readable medium having program code executable by the processor to cause the system to:
obtain fluid property values for a second wellbore fluid sampled at a second depth in a wellbore, wherein the second wellbore fluid comprises at least one of a reservoir fluid and a second contaminant; and
determine a fluid composition value for the second wellbore fluid based, at least in part, on the contaminant reference data.

* * * * *